United States Patent [19]
Stefano et al.

[11] Patent Number: 5,705,185
[45] Date of Patent: *Jan. 6, 1998

[54] TRANSDERMAL DELIVERY OF ESTRADIOL AND PROCESS FOR MANUFACTURING SAID DEVICE

[75] Inventors: Francisco Jose Evaristo Stefano; Jose Adrian Nowogrodski, both of Buenos Aires; Dario Norberto Ramon Carrara, Hurlingham Provence of Buenos Aires, all of Argentina

[73] Assignee: Beta Pharmaceuticals Co., Montevideo, Uruguay

[*] Notice: The term of this patent shall not extend beyond the expiration date of Pat. No. 5,518,734.

[21] Appl. No.: 584,006

[22] Filed: Jan. 11, 1996

Related U.S. Application Data

[63] Continuation-in-part of Ser. No. 210,319, Mar. 2, 1993, Pat. No. 5,518,734, which is a continuation of Ser. No. 938,776, Sep. 2, 1992, abandoned, which is a continuation-in-part of Ser. No. 766,440, Sep. 25, 1991, abandoned.

[51] Int. Cl.[6] .............................................. A61F 13/00
[52] U.S. Cl. ........................................ 424/448; 424/449
[58] Field of Search ................................. 424/448, 449

[56] References Cited

U.S. PATENT DOCUMENTS

| | | | |
|---|---|---|---|
| 4,379,454 | 4/1983 | Campbell et al. | 424/448 |
| 4,537,776 | 8/1985 | Cooper | 514/424 |
| 4,764,381 | 8/1988 | Bodor et al. | 424/449 |
| 4,814,168 | 3/1989 | Sablotsky et al. | 424/78 |
| 4,855,294 | 8/1989 | Patel et al. | 514/212 |
| 4,863,970 | 9/1989 | Patel et al. | 514/784 |
| 4,885,174 | 12/1989 | Bodor et al. | 424/449 |
| 4,954,487 | 9/1990 | Cooper et al. | 514/159 |
| 4,973,468 | 11/1990 | Chiang et al. | 424/449 |
| 4,994,267 | 2/1991 | Sablotsky | 424/78 |
| 5,023,084 | 6/1991 | Chien et al. | 424/448 |

FOREIGN PATENT DOCUMENTS

| | | | |
|---|---|---|---|
| 0 137 278 A2 | 4/1985 | European Pat. Off. | A61K 47/00 |
| 0 169 214 B1 | 1/1986 | European Pat. Off. | A61K 31/57 |
| 0 171 742 | 2/1986 | European Pat. Off. | |
| 0 196 769 A2 | 10/1986 | European Pat. Off. | A61L 15/03 |
| 0 261 429 | 3/1988 | European Pat. Off. | |
| 0 259 136 A2 | 3/1988 | European Pat. Off. | A61L 15/03 |
| 0 268 220 A2 | 5/1988 | European Pat. Off. | A61K 47/00 |
| 0 268 218 A2 | 5/1988 | European Pat. Off. | A61K 47/00 |
| 0 272 918 A2 | 6/1988 | European Pat. Off. | A61M 15/03 |

(List continued on next page.)

OTHER PUBLICATIONS

Cooper, E.R., "Increased Skin Permeability for Lipophilic Molecules," *Journal Pharmaceutical Sciences*, 73(8):1153–1156, (1984).

Idson, B., "Dermatological Emulsions," *Cosmetics & Toiletries, Creams and Lotions*, 95:59–62 (Mar. 1980).

Mollgaard et al., "Vehicle Effect On Topical Drug Delivery" II. Concurrent skin transport of drugs and vehicle components, *Acta Pharm. Suec.* 20:443–450 (1983).

Biological Abstracts, vol. 88, nr. 1, 1989, abstract nr 9062, Philadephia, PA, US; goodman et al.: "Action of penetration enhancers on skin as assessed by the permeation of model drug 5–fluorouracil and estradiol", & J. Invest. Darmatol. 91(4): 323–327, 1988.

Proceed. Intern. Symp. Control. Rel.Bioact. Mater. 14 (1987) pp. 101–102.

*Primary Examiner*—D. Gabrielle Phelan
*Attorney, Agent, or Firm*—Darby & Darby

[57] ABSTRACT

The present invention relates to a transdermal delivery device for estradiol where the metabolic degradation of estradiol to estrone during permeation is inhibited by another substance in the transdermal delivery device. The transdermal device also includes a compound for enhancing the rate of estradiol permeation. The transdermal delivery device containing the inhibitor and enhancer can also be used to simultaneously deliver both estradiol and a progestin at therapeutic rates.

29 Claims, 11 Drawing Sheets

FOREIGN PATENT DOCUMENTS

| | | | |
|---|---|---|---|
| 0 280 413 A1 | 8/1988 | European Pat. Off. | A61L 15/03 |
| 0 288 336 A1 | 10/1988 | European Pat. Off. | A61K 9/70 |
| 0 285 563 A1 | 10/1988 | European Pat. Off. | A61K 31/565 |
| 0 328 806 A2 | 8/1989 | European Pat. Off. | A61K 9/70 |
| 0 341 202 A1 | 11/1989 | European Pat. Off. | A61K 47/00 |
| 0 379 045 A1 | 7/1990 | European Pat. Off. | A61L 15/44 |
| 32 05 258 A1 | 9/1982 | Germany | A61M 37/00 |
| 39 33 460 A1 | 4/1991 | Germany | A61L 15/44 |
| 2 158 355 | 11/1985 | United Kingdom | A61K 47/00 |
| 2 208 147 | 3/1989 | United Kingdom | A61L 15/03 |
| 87/01291 | 3/1987 | WIPO | A61L 15/03 |
| 8 703 490 | 6/1987 | WIPO . | |
| 88/01496 | 3/1988 | WIPO | A61F 13/00 |
| 89/07951 | 9/1989 | WIPO | A61L 15/03 |
| 9 006 120 | 6/1990 | WIPO . | |

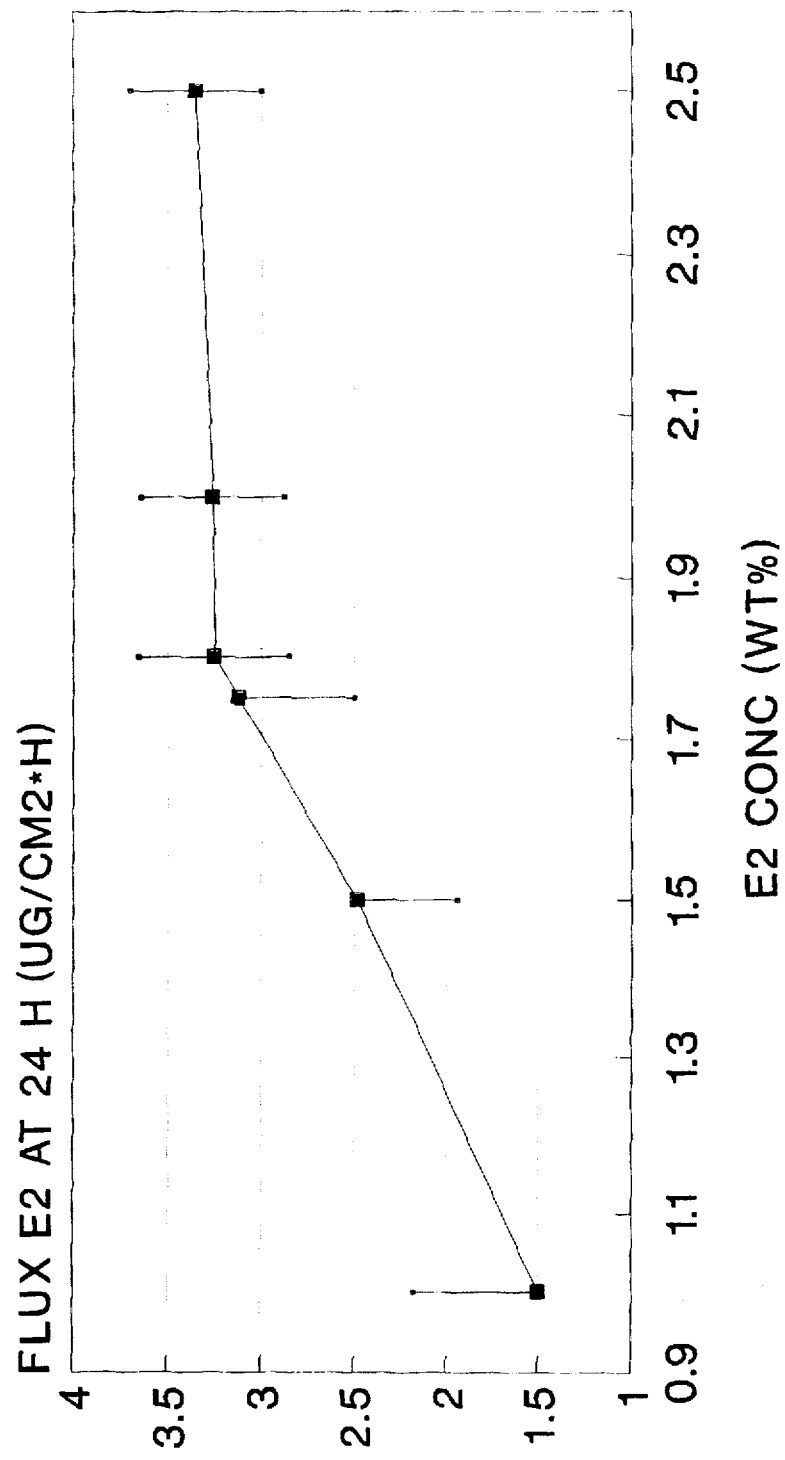

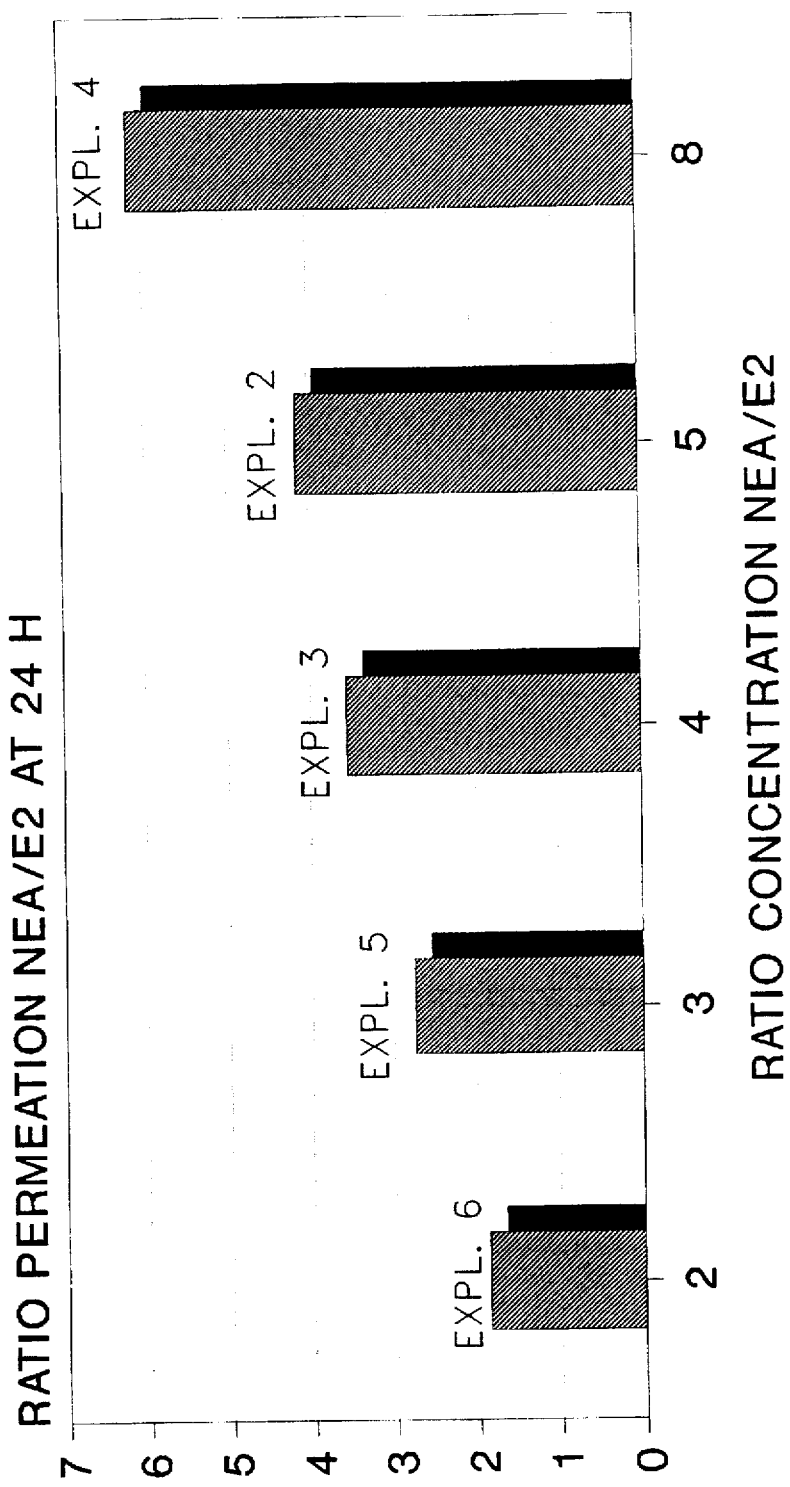

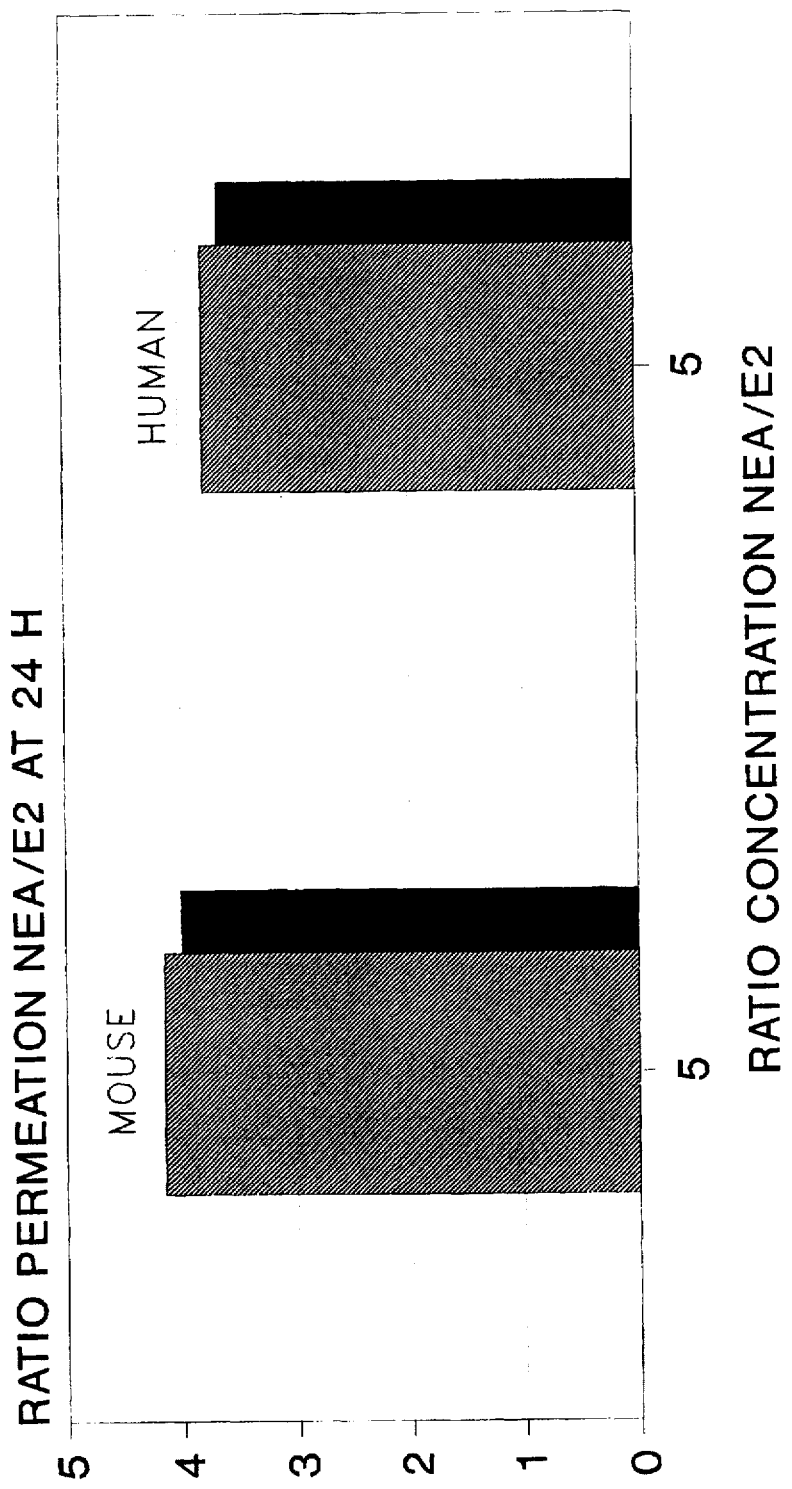

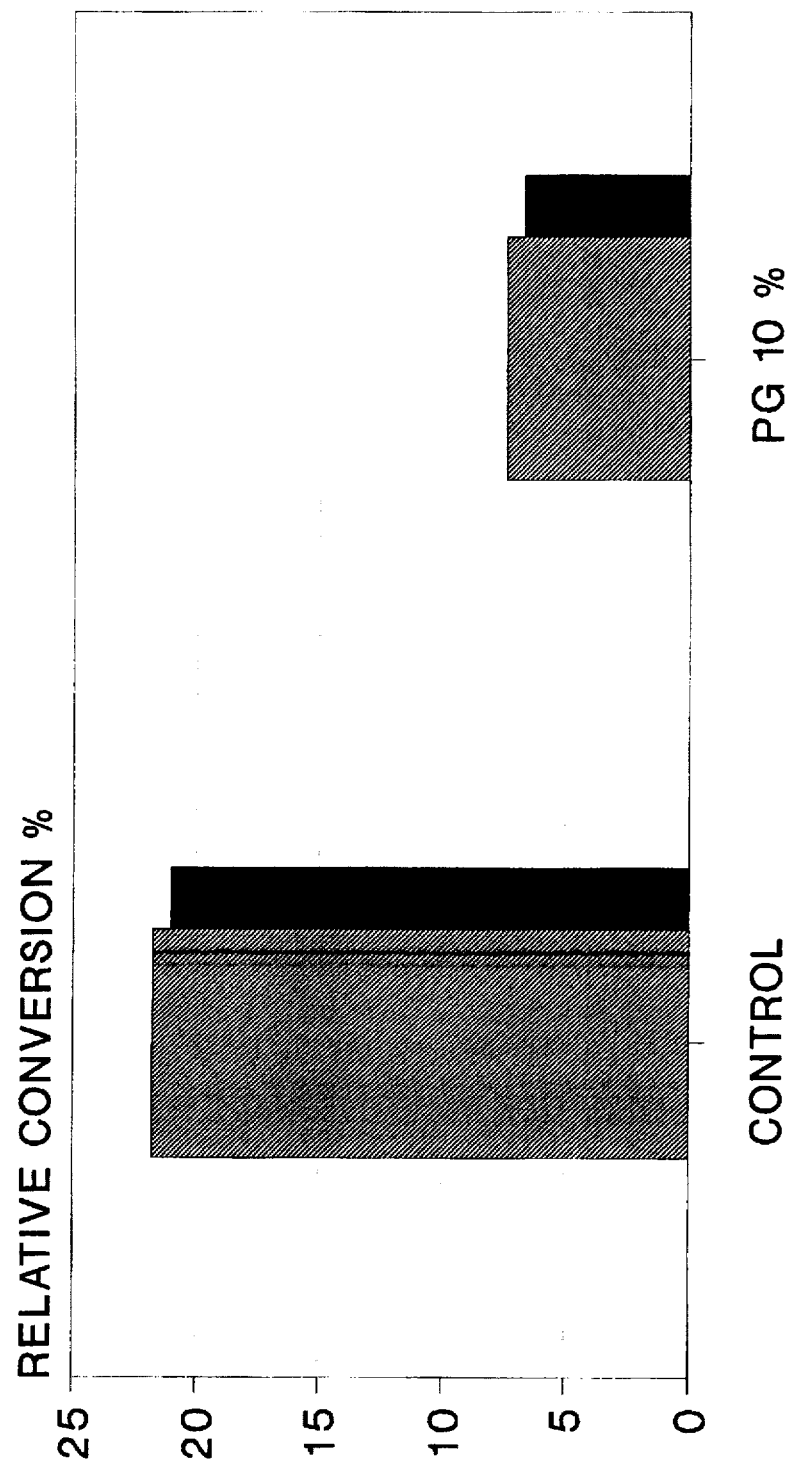

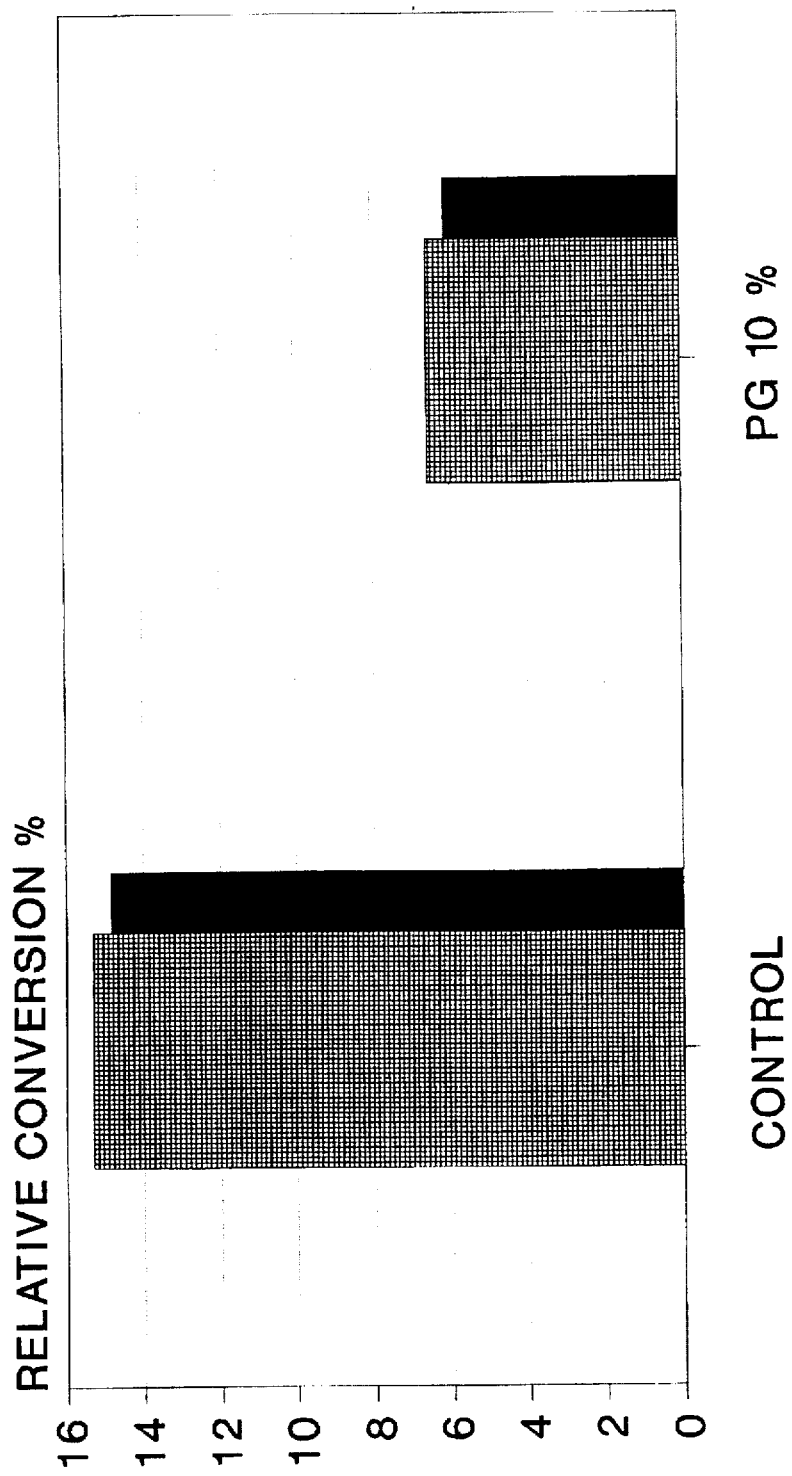

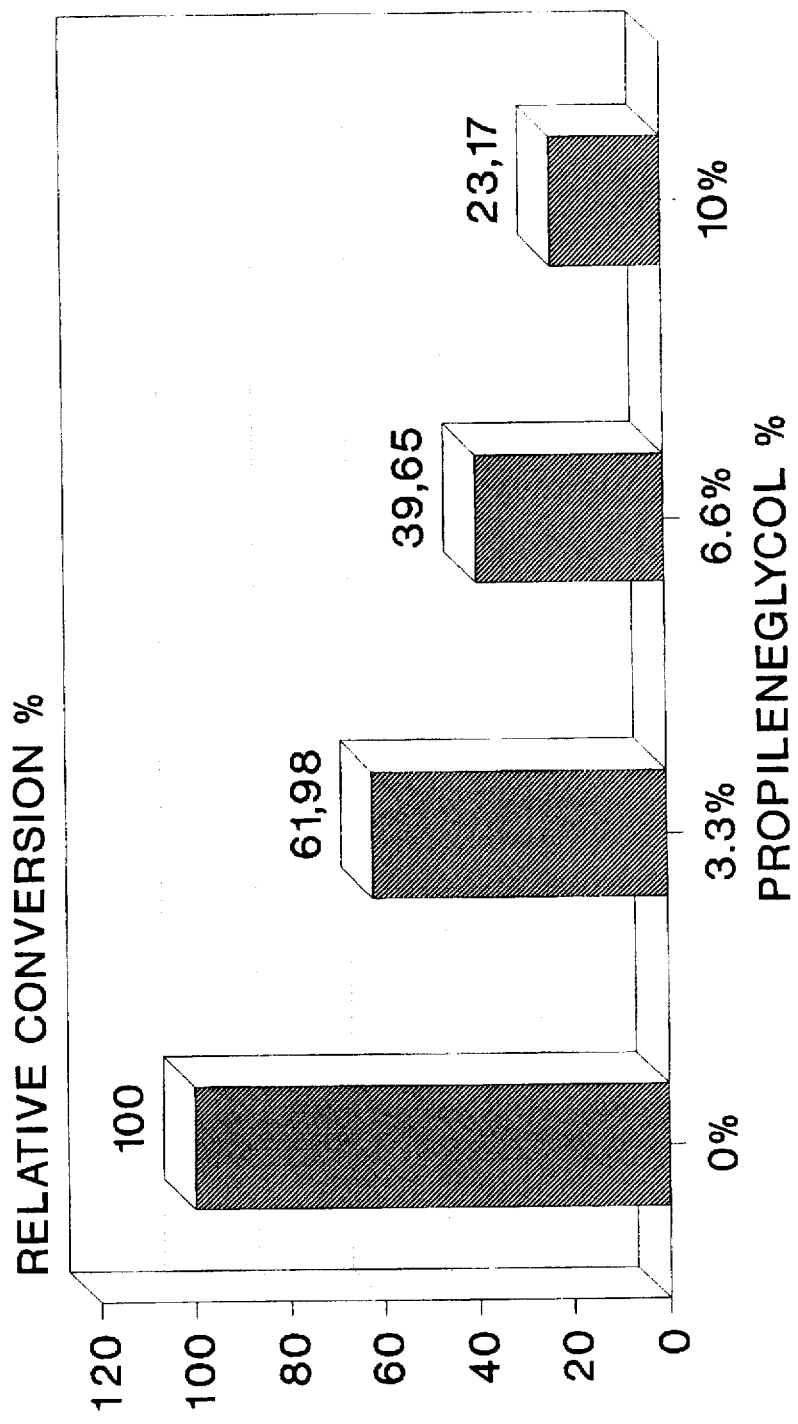

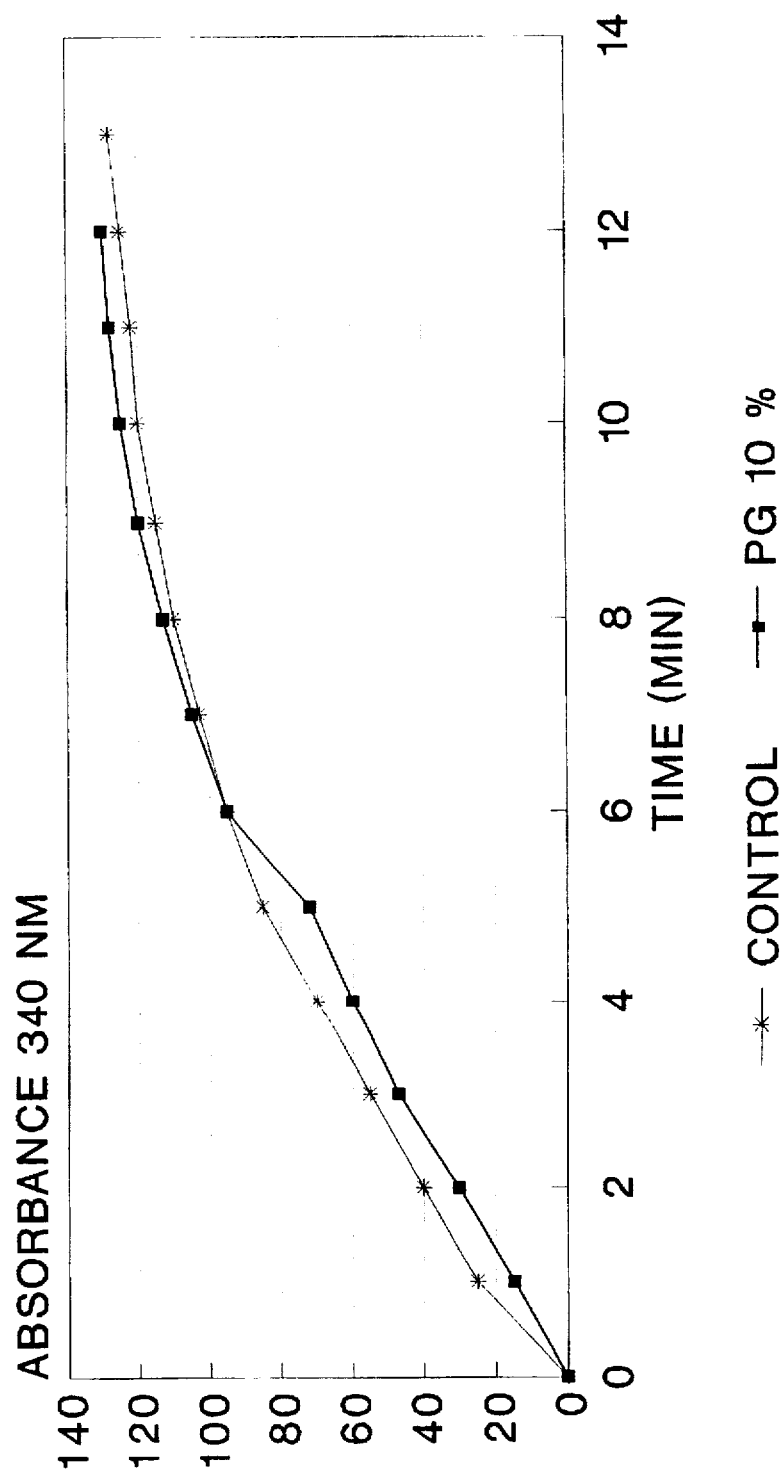

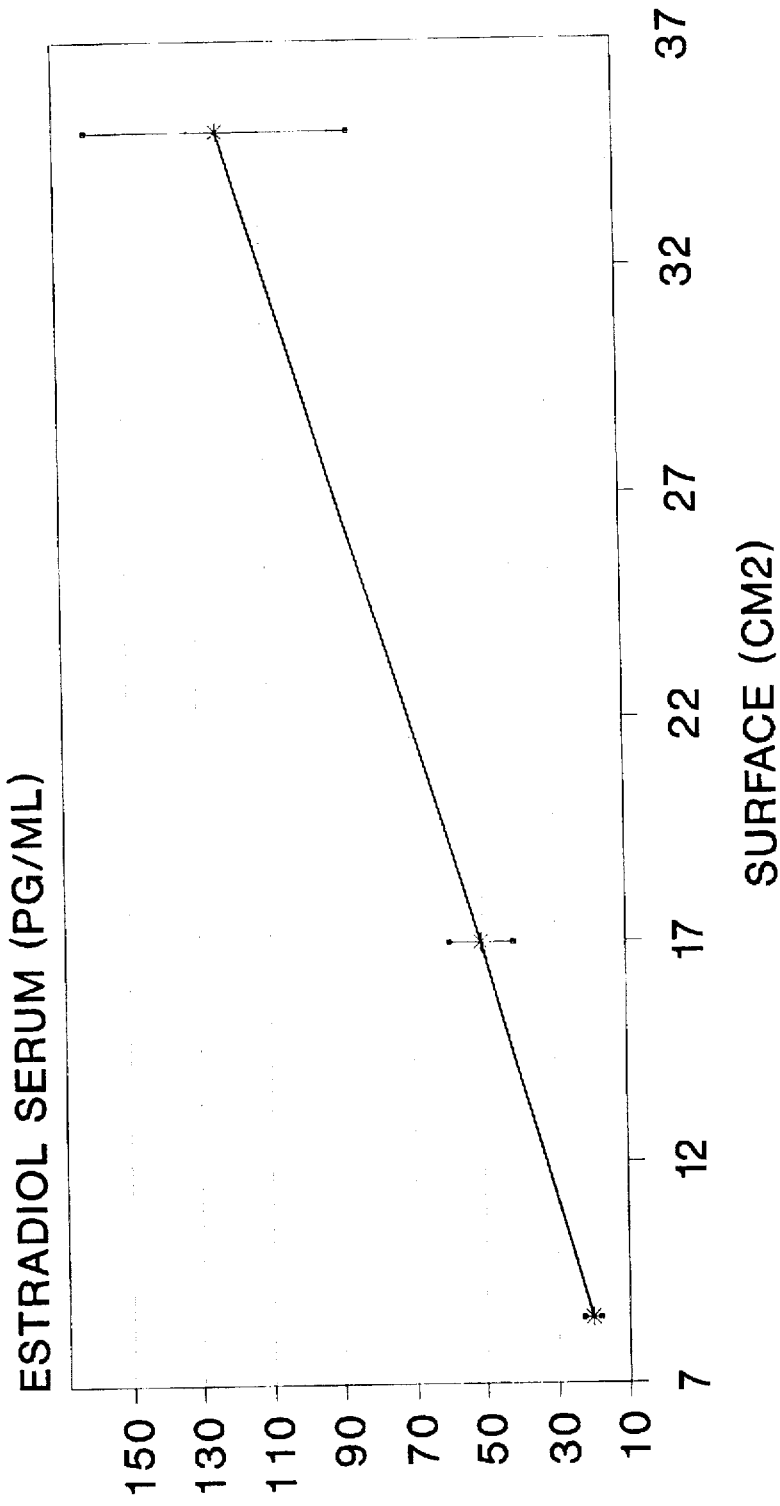

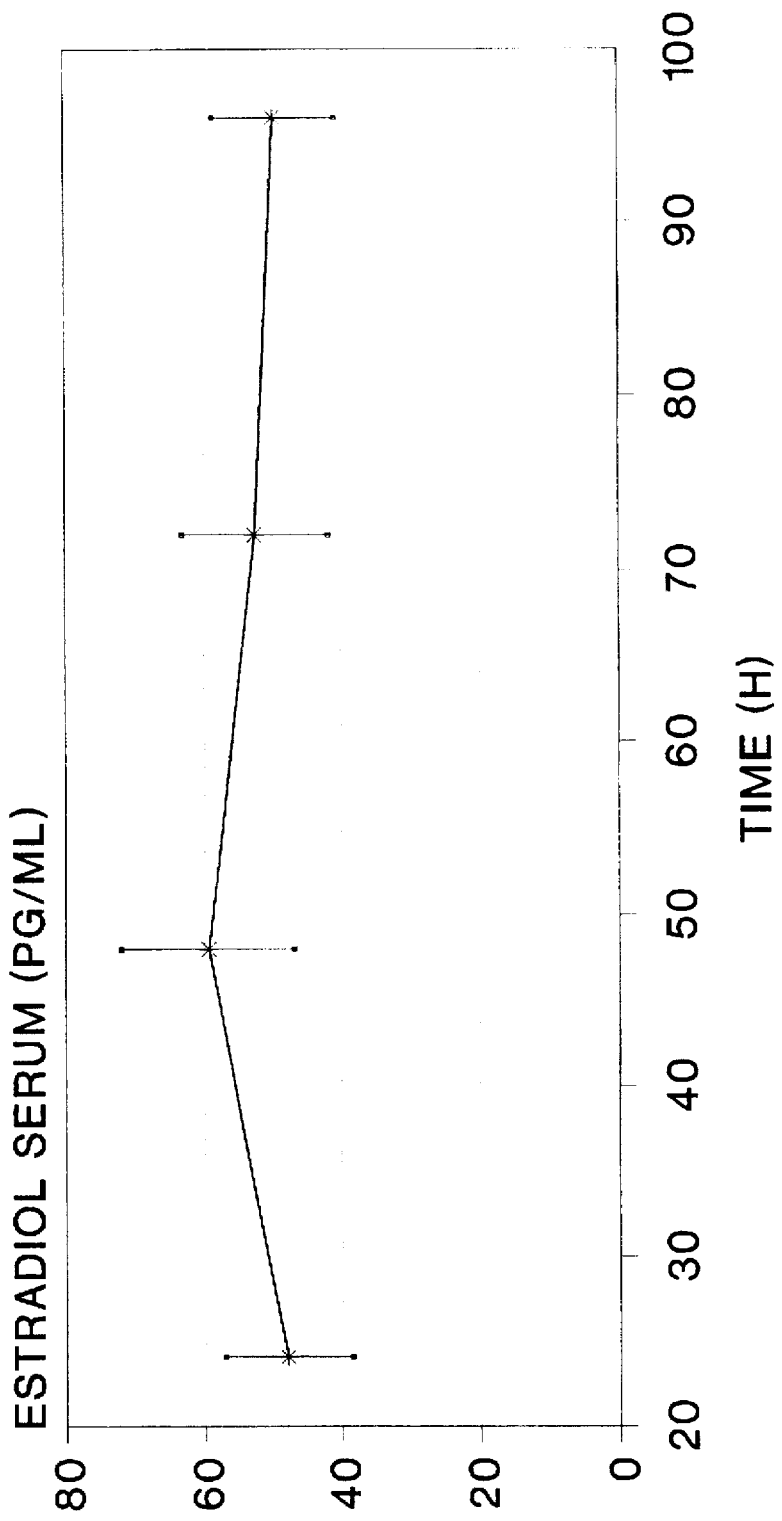

TRANSDERMAL DELIVERY OF ESTRADIOL AND PROCESS FOR MANUFACTURING SAID DEVICE

The application is a continuation-in-part of U.S. application Ser. No. 08/210,319 filed on Mar. 2, 1993 now U.S. Pat. No. 5,518,734, which is a continuation of U.S. application Ser. No. 07/938,776 filed Sep. 2, 1992 (abandoned); which in turn is a continuation-in-part of U.S. application Ser. No. 766,440 filed Sep. 25, 1991 (abandoned).

FIELD OF THE INVENTION

The present invention relates to a device or system (hereinafter "device") for the administration of estradiol by the transdermal or percutaneous route, and to a process for manufacturing said device.

Most particularly to a device for the transdermal administration of estradiol that includes an inhibitor of the enzymatic degradation of estradiol to estrone in the skin, but is chemically compatible with estradiol.

Also the system is versatile enough to allow the incorporation of a progesteron derivative such as norethindrone acetate. Such incorporation results in an alternative device that delivers simultaneously and without interference estradiol and norethindrone acetate at a therapeutically rate.

DESCRIPTION OF THE PRIOR ART

The transdermal or percutaneous administration of drugs provides a new and useful alternative to classical methods, and has been developed since 1960 (R. W. Baker and J. Farrant "Patents in transdermal drug delivery", Drug Delivery Systems 1987 Conference Proceedings) for the systematic treatment of various medical conditions to provide constant and efficient levels of nitroglycerin in the blood (U.S. Ser. No. 806257 filed Nov. 6th 1985, U.S. Ser. No. 275215 filed 19th Apr. 1985/85 and U.S. Pat. No. 3,996, 934); and also to administer various types of steroids, such ethynyl estradiol (EPA 0279282), estradiol (U.S. Ser. No. 806257), and various anti-inflammatories (EPA 0267617), for example.

All known devices have in common a bandage of flexible substrate, a protective release film and a layer in which the active ingredient is dispersed in a vehicle which, in certain cases, contains adhesive components ("adhesive device") and in other cases an adhesive material is provided in an external layer and the active ingredient is contained in a separate layer or intermediate matrix (these devices are called respectively "monolithic devices" and "reservoir devices", see R. W. Baker et. al supra).

With the devices proposed and developed in the prior art, adjuvants known as "increasers", or "enhancers" or "permeation enhancers" are also included for increasing the rate for permeation of the active ingredient. In addition to dimethyl-sulfoxide and azone (1-dodecylhexahydro-2H-azepin-2-one) (EPA 0251245), ethanol, propylene glycols, other alcohols, long chained fatty acids, etc., have been also proposed (R. W. Baker et. al supra).

It has now been found that a further transdermal delivery device for estradiol can be obtained and is suitable for the treatment of menopausal disorders such as hot flushes, depression, osteoporosis, having rapid and sustained effects depending on the use of an "enhancer" component such as one compound selected from unsaturated fatty acids ($C_{12}$–$C_{18}$).

Although nowadays there is no doubt about the need of estradiol replacement therapy for at the prevention of a number of risks associated with estrogen deprivation, several authors have proposed the use of estrogen-progestogen combination to lower the incidence of hyperplasia and/or carcinoma of the uterus (Are fixed dose estrogen-progestogen combinations ideal for all HRT users?, D. Fraser, M. I., Whitehead, J. Endacott, J. Morton, T. A. Ryder, J. Pryse-Davids, British J. Obstetrics and Gynecology, July 1989, Vol. 96, pp 776–782).

Further it has been shown that this combination does not reduce the benefit of estrogen therapy when either osteoporosis or cardiovascular diseases are considered (Reversal of postmenopausal vertebral bone loss by oestrogen and progestogen: a double blind placebo controlled study, N. Munk-Jensen, S. Pors Nielsen, E. B. Obel, P. Bonne Eriksen, British Medical Journal 9 Apr. 1988, Vol. 296, pp 1150–1152.)

This protective effects of progestogens on the estrogen action, makes desirable the design of a combined transdermal system that permit the simultaneous administration of both hormones. This has been revealed by Chien Y. W. in WO 88/01496 U.S. Pat. 8,702,142 discloses about a silicon polymer matrix device that contains in a reservoir a estrogen such as 17-β-estradiol or ethinyl estradiol and a progestin such as levonorgestrel, norethindrone or norethynodrel. This type of device is a transdermal device for controlling fertility.

In the UK patent application 6B-2,208.147 A discloses about a transdermal therapeutic system for the combined administration of oestrogen and gestagens. This devices is a reservoir containing essential constituents of the active ingredient formulation and optionally a membrane.

One object is to obtain also a transdermal device that could deliver at controlled rates both an estrogen and progestogen combined with the appropriate permeation enhancers. This is very important since it is well known that transdermal permeability is mainly influenced by both physicochemical properties of the permeants and by the interaction of the permeants with the enhancers. So a given enhancer could prove to be very satisfactory for an hormone and simultaneously would not increase the permeability of the other hormone. This is well illustrated by Chien in its chapter on "Developmental Concepts and Practice in Transdermal Therapeutic Systems"; Chien Y. W. in Transdermal Controlled Systemic Medications, Marcel Deckker Inc., New York, 1987, pages 25–81, Table VII.

Also B. Idson, Cosmetic & Toileteries 95, 59 (1980) states that the factors affecting drug penetration and, consequently, in most cases effectiveness are complex. He observes that the vehicle that provides ideal conditions for one drug may prove unsatisfactory for another.

SUMMARY OF THE INVENTION

This invention relates to a transdermal delivery device for estradiol whereby metabolic degradation of estradiol to estrone during the permeation is inhibited to a large extent.

Our research in the field of stability or transformation of estradiol in the process of permeation through skin have demonstrated that estradiol is enzymatically oxidazed to estrone when is in contact with the enzimes of the skin.

Is one object of the present invention a transdermal delivery device for estradiol including a flexible substrate and a releasable protective film, the protected surface of said flexible substrate being at least partly covered with a coating layer containing:

a) a dermatologically or pharmaceutically pressure sensitive adhesive material for receiving the device to the skin.

b) estradiol homogeneously distributed in said coating layer as a pharmacologically active ingredient.

c) one compound as an inhibitor of metabolic oxidation of estradiol to estrone.

d) a component which enhances the rate of estradiol permeation.

The compound as an inhibitor of metabolic oxidation of estradiol to estrone is selected from glycerin and ($C_3$–$C_6$) alkylene 1,2-diols.

The component which enhances the rate of estradiol is a compound selected from unsaturated ($C_{12}$–$C_{18}$) fatty acid.

Another object of the invention proposed is the equilibrated mixture of estradiol/norethindrone acetate that combined with an enhancer and an inhibitor of skin metabolism will deliver both hormones at therapeutic rates so as to obtain simultaneouslly the therapeutic effects of estradiol and the protective action on the uterus of the progestogen.

Other object of the present invention is to provide a delivery device for the transdermal administration of estradiol which allows a high transdermal flux with which it is possible to maintain estradiol at the required constant high level in the blood.

In the preferred embodiment of the present invention the estradiol homogeneously distributed in said coating layer as a pharmacologically active ingredient comprises from 1 to 5 wt % and preferably 2 wt %; the inhibitor of metabolic oxidation of estradiol to estrone selected from glycerin and ($C_3$–$C_6$) alkylene 1,2 diols, comprises from 5 to 30 wt % and preferably 15 wt %, the percentage being based on the total weight of said coating layer and the component which enhances the rate of estradiol permeation comprises from 1 to 20 wt % and preferably 10 wt % of at least one first compound selected from unsaturated ($C_{12}$–$C_{18}$) fatty acids.

Also in said embodiment of the invention, comprises another pharmacologically active agent, a progestin such as levonorgestrel or norethindrone acetate included in the concentration from 2 to 10 wt %.

In another preferred embodiment of the invention, the enhancing component comprises as enhancer, oleic acid and as inhibitor of oxidation, propylene glicol in a ratio of 1:0.5 to 1.5.

It is another object of the present invention a process for manufacturing a transdermal delivery device for estradiol, comprising the steps of providing a coating layer on at least part of one surface of a flexible substrate, said coating layer:

a) a dermatologically or pharmaceutically acceptable pressure sensitive adhesive material for securing the device to the epidermis.

b) estradiol homogeneously distributed in said coating layer as a pharmacologically active ingredient.

c) a component as inhibitor of enzymatic oxidation of estradiol to estrone which comprises 5 to 30 wt % of one compound selected from glycerin and ($C_3$–$C_6$) alkylene 1,2 diols.

d) a component which enhances the rate of estradiol permeation and which comprises from 1 to 20 wt % at least one first compound selected from unsaturated ($C_{12}$–$C_{18}$) fatty acids, the percentages being based on the total weight of said coating layer; and providing a releasable protective layer which, in the finished device, lies on the opposite side of the coating layer to the flexible substrate.

BRIEF DESCRIPTION OF THE FIGURES

FIG. 2 is a graph depicting the results of the permeation studies using mouse skin models.

FIG. 3A depicts the results of Examples 3–7 where the permeation ratio of norethindrone acetate/estradiol into mouse skin can be modified by modifying the concentration ratio of norethindrone acetate and estradiol in the transdermal devices.

Figure 1A:
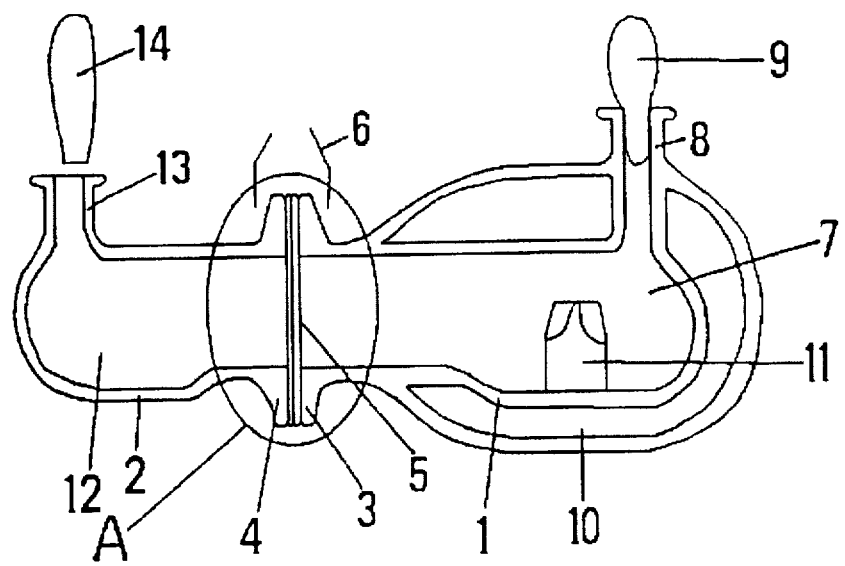
FIG. 1A is a schematic drawing of the diffusion chamber used for in vitro permeation experiments with mouse and human skin.

"Penetration enhancement" or "permeation enhancement" as used herein relates to an increase in the permeability of skin to a pharmacologically active agent.

By the term "transdermal" as used herein refer to delivery by passage of the drug through the skin into the bloodstream.

"Pharmacologically active agent" or "drug" as used herein is meant any chemical material or compound suitable for transdermal administration which induces a desired systemic effect.

By "toxicologically or pharmaceutically acceptable" as used herein is meant the pharmaceutical actives as well as the other compatible drugs, medicaments, adhesive components or inert ingredients which are suitable for use in contact with the tissues of humans and lower animals without undue toxicity, irritation and allergic response.

In one aspect, the present invention provides a transdermal delivery device for estradiol comprising a flexible substrate and a releasable protective film, the protected surface of said flexible substrate being at least partly covered with a coating layer containing (a) a dermatologically or a pharmaceutically acceptable pressure sensitive adhesive material for securing the device to the skin, (b) estradiol homogeneously distributed as a pharmacologically active ingredient and (c) a component which enhances the rate of estradiol permeation and which comprises from 1 to 20 wt % of at least one compound selected from unsaturated ($C_{12}$–$C_{18}$) fatty acids, and from 5 to 30 wt % of an inhibitor of metabolic oxidation of estradiol to estrone selected from glycerin and ($C_3$–$C_6$) alkylene 1,2 diols, the percentages being based on the total weight of said coating layer.

The estradiol is preferably present in an amount exceeding its saturation concentration in said coating layer.

That was confirmed by the following experiment: A different concentration of estradiol in the coating layer was tested in the permeation studies (mice skin models). The techniques of this permeation studies is described afterwards.

The results of this experiments is shown in Table I and FIG. 2.

TABLE I

| Estradiol concentration wt % | Flux through mouse skin at 24h µg/cm$^2$*h |
|---|---|
| 1 | 1.8 ± 0.29 |
| 1.5 | 2.2 ± 0.25 |
| 1.75 | 2.8 ± 0.33 |
| 1.8 | 3.28 ± 0.41 |
| 2 | 3.31 ± 0.45 |
| 2.5 | 3.39 ± 0.37 | n = 4

Assuming the flux through the skin as a membrane limited transport, increasing the concentration of dissolved drug causes a proportional increase in this flux. This continues until the saturation concentration in the system is reached (solubility limit). At concentrations higher than this solubility there is no change in flux and the excess non dissolved solid drug functions as a reservoir and helps to maintain a constant flux of drug for a prolongs period of time. The same concept was illustrated by Joel L. Zatz in Drug Development and Industrial Pharmacy 9 (4), 561–577 (1983).

In our cases the solubility limit is 1.8 wt % of estradiol. An increase of the concentration above 2.1 wt % produce precipitation of estradiol in the polymeric matrix, this produces bad appearance and diminished the excellent adhesive properties of the patch obtained when the estradiol was completely dissolved.

In other aspect, the present invention provides a process for manufacturing the transdermal delivery device for estradiol, comprising the steps of providing a coating layer on at least part of one surface of a flexible substrate, said coating layer containing (a) a dermatologically or pharmaceutically acceptable pressure sensitive adhesive material for securing the device to the epidermis, (b) estradiol homogeneously distributed as a pharmacologically active ingredient and (c) and a component which enhanced the rate of estradiol permeation and which comprises from 1 to 20 wt % and preferably 10 wt % of at least one compound selected from unsaturated ($C_{12}$–$C_{18}$) fatty acids and alkyl esters thereof, and (c) a compound which inhibited the enzymatic oxidation of estradiol to estrone, glycerin and ($C_3$–$C_6$) alkylene 1,2 diols, added from 5 to 30 wt % and preferably 15 wt %, the percentages being based on the total weight of said coating layer; and providing a releasable protective layer which, in the finished device, lies on the opposite side of the coating layer to the flexible substrate.

Preferably, the amount of estradiol in said coating layer is in excess of the saturation concentration therein.

Advantageous, the coating layer is provided by coating it on the releasable protective layer, eg a silicone layer, bringing the flexible substrate into contact with the coating layer, and then cutting the resultant structure to the required shape and size, and then packaging in a convenient blister system.

The releasable protective layer is discarded immediately before the device is applied to the skin of a patient. Obviously, the formulation of the coating layer, particularly the adhesive material, is not only dermatologically acceptable but also pharmacologically acceptable.

The adhesive material may be selected from a wide variety of pressure sensitive adhesive materials such as silicones, rubber, PIB (polyisobutylene) and acrylic adhesives.

A reinforcing component (solid) which may be selected from the polyterpene resins, such as modified colophony resins such as Pentalyn (an esterified colophony resin with pentaerythritol), etc., may also be included.

Amongst materials suitable for the flexible substrate, cellophane (cellulose xantate film), Saran (polyvinylidene chloride film), polyvinyl chloride, polyethylene, polypropylene, polyurethane, polyesters such as polyethylene terephthalate including binary structures such as alunimum-polyethylene coatings, polyester-polyethylene coatings, etc., may be used.

For the releasable protective layer, any of the above mentioned coatings for the substrate can be used, preferably polyesters, such as polyethylene terephtalate, etc. covered with a silicone to prevent sticking of the adhesive.

The blister package is a packaging configuration capable of providing excellent environmental protection coupled with an aesthetically pleasing and efficacious appearance. The chemical and physical stability studies performed in this packaging under three storage conditions, i.e., 25°, 37° and 45° C.; have established excellent chemical and physical stabilities.

This package mode is formed by heat softening a sheet of thermoplastic resin and vacuum drawing the softened sheet of plastic into a contoured mold. After cooling the sheet is released from the mold and proceeds to the filling station of the packaging station, where is filled with product and then lidded with a heat sealable backing material.

The backing material is usually heat seal coated aluminum foil. Materials commonly used for the thermoformable blister are polyvinylchloride (PVC), PVC/polyethylene combinations, polystyrene and polypropylene. For added moisture protection, polyvinylidene chloride (saran) or polychlorotrifluoroethylene (Aclar) can be used.

An amount of estradiol in the adhesive matrix of from 1 to 5 wt %, preferably 2 wt % based on the total weight of the coating layer adhesive matrix, is sufficient for the purpose of this invention. The amount of estradiol preferably exceeds the saturation concentration thereof in said coating layer in order to keep the flux at a constant rate and thereby maintain a more constant level of estradiol in the blood. Indeed, it is possible to formulate coating layers without reaching saturation levels if the required dosage and the estradiol levels so require it.

The estradiol permeation enhancing component performs a vital role in the maintenance of constant systemic levels of estradiol.

The above mentioned alkylene diols and, particularly propylene glycol, have been proved to be an inhibitor of the skin metabolism degradation of estradiol to estrone, that is to say, the skin not only has a passive role recognized as protector against the penetration of exogenous agents, since it has been demonstrated as being a metabolizer of certain substances, among them estradiol which undergoes enzymatic degradation to estrone.

Tests conducted by the applicant have shown that propyleneglycol inhibits the enzymatic mechanism that causes degradation of estradiol to estrone. Therefore, the propyleneglycol and other low chain alkylenediols at the concentrations added complement the enhancer effect of the fatty acids by avoiding or reducing estradiol degradation, thereby enabling systemic estradiol levels to be obtained which are higher than those obtainable by conventional transdermal delivery devices which operate without blocking said enzymatic mechanism, but which use, for example, oleic acid as "enhancer", as will be appreciated from Table II hereinafter.

The present invention will be further described in the following Examples.

EXAMPLE 1

Preparation of formulas containing estradiol.
A) Preparation of an adhesive mixture.

To a vinyl-acrylic multipolymer adhesive solution diluted with ethanol/toluene/ethyl acetate to 33 wt % solids, a solid rosin tackifier component is added with stirring at room temperature for a period of time necessary to obtain a homogeneous mixture (for about 4 hours).

B) Preparation of formula containing estradiol.

To the material prepared in step A) above, whilst stirring, estradiol, the permeation rate enhancer (oleic acid) and the inhibitor of the estradiol degradation (propylene glycol) are added. A clear solution is obtained and kept in a closed vessel to avoid evaporation of the solvent medium until air bubbles have dispersed. Finally, the solution is filtered through a stainless steel sieve (100 mesh).

In this example the quantities used were:

| | |
|---|---|
| Adhesive polymer | 19.64 kg |
| Rosin tackifier | 2.40 kg |
| Estradiol | 0.240 kg |
| Propyleneglycol | 1.80 kg |
| Oleic acid | 1.20 kg |

C) Preparation of the transdermal delivery device.

On a flexible laminate (which later defines the releasable protective layer), the solution prepared as described above, is applied by means of a conventional coating device. Said solution is applied to one of the surfaces of the flexible laminate (which may, for example, be a polyester film previously sprayed with silicon) to form a layer of predetermined thickness, for example 400 micrometers, and is subsequent dried by hot air circulation.

The thus coated siliconised polyester is laminated on a second flexible film which constitutes the substrate in the finished device.

The process ends with cutting to size, for example, by means die cutting of the multi-layer laminate to form shapes of the desired geometry and size. Then the final product is packaged in a thermoformed PVC blister system, which is heat sealed with a lacquered aluminum foil laminate.

The final composition of this example is: adhesive polymer 53 wt %, rosin tackifier 20 wt %, estradiol 2 wt %, propyleneglycol 15 wt %, oleic acid 10 wt %.

EXAMPLE 2

Preparation of formulas containing estradiol and norethisterone acetate.

A) Preparation of an adhesive mixture.

To a vinyl-acrylic multipolymer adhesive solution diluted with ethanol/toluene/ethyl acetate to 33 wt % solids, a solid rosin tackifier component is added with stirring at room temperature for a period of time necessary to obtain a homogeneous mixture (for about 4 hours).

B) Preparation of formula containing estradiol and norethindrone acetate.

To the material prepared in step A) above, whilst stirring, estradiol, norethindrone acetate, the permeation rate enhancer (oleic acid) and the inhibitor of the estradiol degradation (propylene glycol) are added. A clear solution is obtained and kept in a closed vessel to avoid evaporation of the solvent medium until air bubbles have dispersed. Finally, the solution is filtered through a stainless steel sieve (100 mesh).

In our case the quantities used were:

| | |
|---|---|
| Adhesive polymer | 18.68 kg |
| Rosin tackifier | 2.40 kg |
| Estradiol | 0.240 kg |
| Norethindrone acetate | 0.960 kg |
| Propyleneglycol | 1.80 kg |
| Oleic acid | 1.20 kg |

C) Preparation of the transdermal delivery device.

On a flexible laminate (which later defines the releasable protective layer), the solution prepared as described above, is applied by means of a conventional coating device. Said solution is applied to one of the surfaces of the flexible laminate (which may, for example, be a polyester film previously sprayed with silicone) to form a layer of predetermined thickness, for example 400 micrometers, and is subsequent dried by hot air circulation.

The thus coated siliconised polyester is laminated on a second flexible film which constitutes the substrate in the finished device.

The process ends with cutting to size, for example, by means die cutting of the multi-layer laminate to form shapes of the desire geometry and size. Then the final product is packaging in a thermoformed PVC blister system, which is heat sealed with a lacquered aluminum foil laminate.

The final composition of this example is: adhesive polymer 43 wt %, rosin tackifier 20 wt %, estradiol 2 wt %, norethindrone acetate 10 wt %, propyleneglycol 15 wt %, oleic acid 10 wt %.

EXAMPLE 3

This example is similar to example 2, wherein the composition is the follow: adhesive polymer 45 wt %, rosin tackifier 20 wt %, estradiol 2 wt %, norethindrone acetate 8 wt %, propyleneglycol 15 wt %, oleic acid 10 wt %.

EXAMPLE 4

This example is similar to example 2, wherein the composition is the follow: adhesive polymer 46 wt %, rosin tackifier 20 wt %, estradiol 1 wt %, norethindrone acetate 8 wt %, propyleneglycol 15 wt %, oleic acid 10 wt %.

EXAMPLE 5

This example is similar to example 2, wherein the composition is the follow: adhesive polymer 47 wt %, rosin tackifier 20 wt %, estradiol 2 wt %, norethindrone acetate 6 wt %, propyleneglycol 15 wt %, oleic acid 10 wt %.

EXAMPLE 6

This example is similar to example 2, wherein the composition is the follow: adhesive polymer 49 wt %, rosin tackifier 20 wt %, estradiol 2 wt %, norethindrone acetate 4 wt %, propyleneglycol 15 wt %, oleic acid 10 wt %.

EXAMPLE 7

This example is similar to example 2, wherein the composition is the follow: adhesive polymer 45 wt %, rosin tackifier 20 wt %, estradiol 2 wt %, norethindrone acetate 8 wt %, propyleneglycol 15 wt %, elaidic acid 10 wt %.

TRANSDERMAL PERMEABILITY

Furthermore, "in vitro" permeation experiments with abdominal mouse skin and human skin were made using the diffusion chamber that is schematically shown in longitudinal section in FIG. 1.

The diffusion chamber illustrated in FIG. 1 comprises a body having front and rear tubular sections 1 and 2 having respective annular end flanges 3 and 4 by which the sections 1 and 2 are joined together. A sample of skin 5, with attached estradiol delivery device D to be tested facing the rear tubular section 2, is clamped between the flanges 3 and 4 by means of a pinch clamp 6.

The tubular section 1 has an internal chamber 7 with an opening 8 furnished with a glass stopper 9. The tubular section 1 has also a jacket 10 through which warm water can be circulated to maintain the contents of the chamber 7 at the desired temperature. The chamber 7 contains a magnetic bar stirrer 11 which is rotatable by means of a magnetic field applied externally means (not shown) to enable the contents of the chamber 7 to be stirred.

The tubular section 2 has a chamber 12 with an opening 13 furnished with a glass stopper 14.

In the assay, the skin of Swiss mice, shaved 72 hours before the experiments, was employed. Also used was human skin obtained from human skin samples (remnants of plastic surgery) which have been eliminated the adipose tissue by scissors, and then was cut to 500 microns by a dermatome.

Figure 1B:
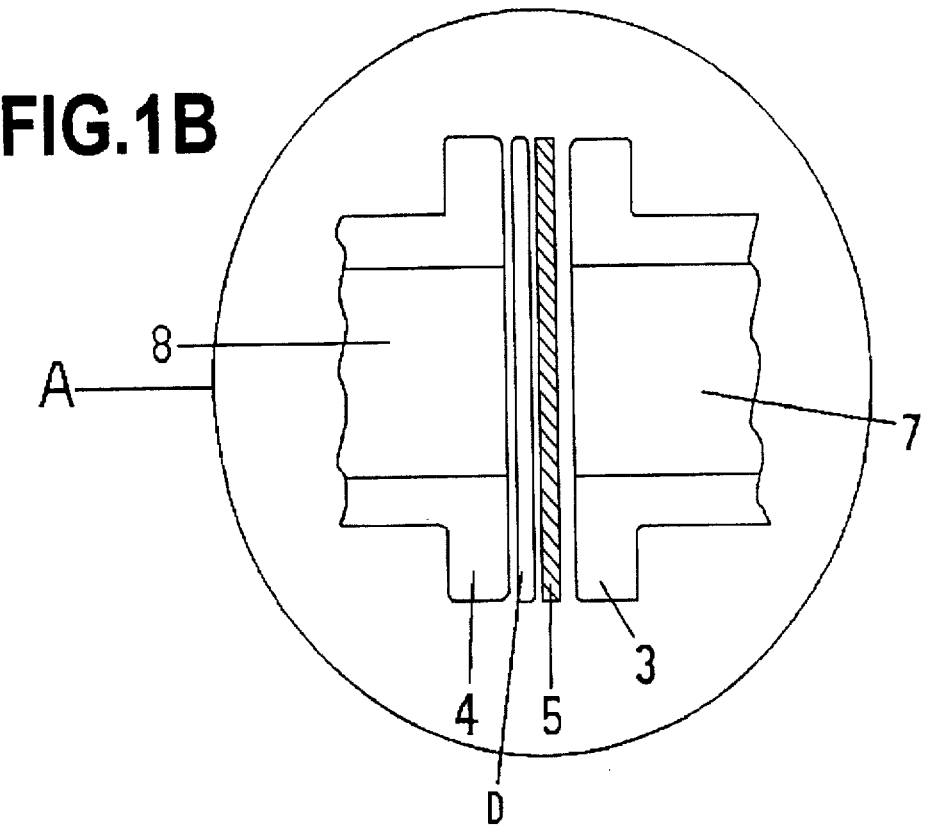
FIG. 1B is a close-up drawing of the clamping section of the diffusion chamber depicted in FIG. 1A.

Both the hairless mouse skin and the human skin with estradiol delivery device attached were clamped between the flanges 3 and 4, as shown the FIGS. 1A and 1B with the dermis towards chamber 12 which is a receptor chamber. Each experiment was started by loading chamber 7 with 5.5 ml of a receptor solution of sodium lauryl sulfate (0.5%), starting the stirrer 11 and taking samples at pre determined periods of time and the subsequent determination of permeated estradiol (by HPLC).

The following Table II illustrates the results obtained in assays performed under the above mentioned conditions using devices as described in the examples.

TABLE III

|  | Estradiol (nmol/ml) | Estrone (nmol/ml) | % Estradiol Metabolized ($E_1*100/E_1 + E_2$) | Inhibition % |
|---|---|---|---|---|
| Exp. 1 |  |  |  |  |
| Control | 2.62 | 0.73 | 21.8 | 66.0 |
| PPG 10% | 3.51 | 0.27 | 7.4 |  |
| Exp. 2 |  |  |  |  |
| Control | 2.94 | 0.53 | 15.3 | 57.2 |
| PPG 10% | 2.71 | 0.19 | 6.55 |  |

Our experimentation demonstrated that the inhibition of the enzymatic conversion of estradiol to estrone by propyleneglycol, is minimized at 10% wt of propyleneglycol. This was shown in FIG. 4C. In another experiment, the effect of several concentrations of propyleneglycol on estradiol metabolism was studied in similar conditions to the above mentioned tests. The results of the experiment are

TABLE II

| Example | Skin Model | Cumulative Estradiol Permeation ($\mu g/cm^2$) | | | | Cumulative Norethindrone Permeation ($\mu g/cm^2$) | | | |
|---|---|---|---|---|---|---|---|---|---|
| | | 24h | 48h | 72h | 96h | 24h | 48h | 72h | 96h |
| 1 | Mouse | 79.4 | 145.1 | 212.3 | 273.7 | | | | |
| 1 | Human | 6.21 | 13.68 | 19.17 | 25.63 | | | | |
| 2 | Mouse | 75.55 | 138.2 | 208.5 | 258.1 | 313.4 | 592.3 | 979.9 | 1190.8 |
| 2 | Human | 5.9 | 12.44 | 18.6 | 23.7 | 22.5 | 52.6 | 89.2 | 110.9 |
| 3 | Mouse | 69.9 | 146.2 | 196.7 | 263.5 | 247.5 | 533.4 | 776.9 | 1027.7 |
| 4 | Mouse | 38.7 | 76.1 | 102.8 | 129.7 | 239.8 | 544.3 | 769.2 | 997.8 |
| 5 | Mouse | 71.9 | 144.1 | 189.9 | 246.1 | 201.3 | 407.8 | 513.3 | 765.4 |
| 6 | Mouse | 67.4 | 152.7 | 191.1 | 215.9 | 127.4 | 323.8 | 376.5 | 477.1 |
| 7 | Mouse | 18.7 | 39.7 | 51.4 | 87.9 | 41.5 | 91.3 | 124.5 | 167.9 |

The association of norethindrone acetate with estradiol in our devices does not impair the permeation rate of the latter as shown by the comparison of the permeation profiles of the transdermal devices containing estradiol and norethindrone acetate.

Another conclusion of the results shown in the table above mentioned is that by modifying the concentration ratio of norethindrone acetate/estradiol we can modify the permeation ratio of norethindrone acetate/estradiol. FIG. 3A and 3B.

With these results we provided the possibility to regulate the dose of estradiol and norethisterone supplied modifying the concentration ratio of norethindrone acetate/estradiol and the surface of devices.

INHIBITION OF THE ESTRADIOL METABOLISM IN HUMAN SKIN

The inhibition of the mechanism of the enzymatic degradation from estradiol to estrone by propyleneglycol has been studied using the same device illustrated in FIG. 1 as follows:

Stratum corneum was eliminated with a surgical knife at 37° C.

CONTROL: Saturated solution of estradiol in saline solution.

Figure 8:
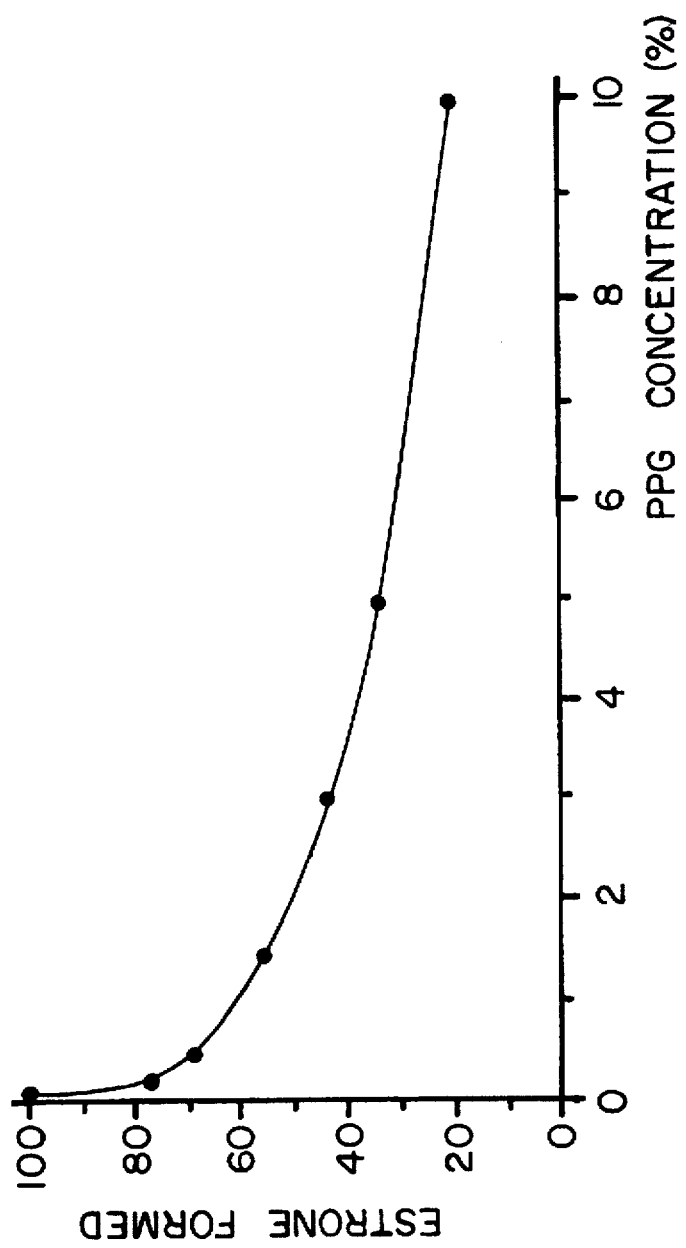

PPG: Saturated solution of estradiol in saline solution+3.3%, 6.6% and 10% PPG. The results of two sets of experiments are shown in Table III (n=3), and FIGS. 4A and 4B.

shown in Table IVa and FIG. 8. Said results are expressed as a percent of estradiol conversion to extrone.

TABLE IVa

| Inhibitory effect of different concentration of propyleneglycol (PG) on estradiol conversion to estrone | | | | | | |
|---|---|---|---|---|---|---|
| | PG 10% | PG 5% | PG 3% | PG 1.5% | PG 0.5% | PG 0.25% |
| % estrone formed | 48.3% n = 12 | 9.2% n = 4 | 16.1% n = 4 | 20.6% n = 4 | 26.8% n = 4 | 33.6% n = 4 | 37.9% n = 4 |

17-β-estradiol dehydrogenase is the enzyme catalyzing conversion of estradiol to estrone, Davis et. al H. Biol. Chem. 247, 1407 (1972) found that the enzyme located in microsomes of rat skin have a preference for $NAD^+$ as cofactor.

Another experimentation in this field was carried out using purified 17-β-hydroxysteroid dehydrogenase, 17-β-estradiol as a substrate and $NAD^+$ as a cofactor in the control tubes, in sample tubes 10% in volume of propyleneglycol was added. The continuous monitoring of the increase in the absorbance at 340nm generated by the appearance of NADH was the method used. No differences were obtained between control and propyleneglycol. This results was shown in Table IV and FIG. 5. Therefore the inhibition of the conversion is no mediated by a denaturalization process of the enzyme, therefore we postulated that the process of inhibition was governed by competition for NAD⁺.

TABLE IV

| Time (min) | Control | Propylene glycol 10% |
|---|---|---|
| 0 | 0 | 0 |
| 1 | 25 | 15 |
| 2 | 40 | 30 |
| 3 | 55 | 47 |
| 4 | 70 | 60 |
| 5 | 85 | 72 |
| 6 | 95 | 95 |
| 7 | 103 | 105 |
| 8 | 110 | 113 |
| 9 | 115 | 120 |
| 10 | 120 | 125 |
| 11 | 122 | 128 |
| 12 | 125 | 130 |

ESTRADIOL BIOAVAILABILITY OF TRANSDERMAL ADMINISTRATION OF ESTRADIOL

The rate of estradiol permeation in the formulation according to the present invention, was examined "in vivo" by measuring the estradiol blood level in 6 voluntary post-menopausal women, using devices of different surfaces as described in Example 1, estradiol concentration being measured in the blood serum 24 hours after application. The techniques used to measuring estradiol was radioinmoassays (RIA).

The Table V and FIG. 6 illustrates the results obtained.

TABLE V

| Device surface (cm²) | Estradiol level in plasma (pg/ml) |
|---|---|
| 8.5 | 20.5 ± 2.4 |
| 17 | 50.5 ± 9.1 |
| 35 | 121.8 ± 37.2 |
| | (means values ± SEM) |

The experiment was repeated with the device of Example 1 cut to 17 cm² to verify the amount of estradiol accumulated in the blood plasma, in assays lasting 96 hours. This results was shown in the follow Table VI and FIG. 7.

TABLE VI

| Time | Estradiol level (pg/ml) |
|---|---|
| 24 hours | 47.7 ± 9.3 |
| 48 hours | 59.3 ± 12.6 |
| 72 hours | 52.4 ± 10.7 |
| 96 hours | 49.6 ± 8.9 |
| | (mean values ± SEM) |

We claim:

1. A transdermal delivery device for estradiol including a flexible substrate and a releasable protective film, the protected surface of said flexible substrate being at least partly covered with a coating layer containing:

(a) a dermatologically or pharmacologically acceptable pressure sensitive adhesive material;

(b) estradiol homogeneously distributed in said coating layer as a pharmacologically active ingredient;

(c) one compound as an inhibitor of metabolic oxidation of estradiol to estrone, said compound selected from the group consisting of glycerin and ($C_3$–$C_6$) alkylene 1,2-diols;

(d) a second compound which enhances the rate of estradiol permeation, said second compound selected from the group consisting of unsaturated ($C_{12}$–$C_{18}$) fatty acids; and (e) a pharmacologically active progestin.

2. A transdermal delivery device for estradiol comprising a flexible substrate and a releasable protective film, the protective surface of said flexible substrate being at least partly covered with a coating layer containing:

a) a dermatologically or pharmacologically acceptable pressure sensitive adhesive material for securing the device to the skin;

b) estradiol homogeneously distributed in said coating layer as a pharmacologically active ingredient, said estradiol comprising from 1 to 5 wt. %;

c) one compound as an inhibitor of metabolic oxidation of estradiol to estrone, said compound selected from the group consisting of glycerin and ($C_3$–$C_6$) alkylene 1,2 diols in a concentration from 0.25 to 30 wt %;

d) a second compound which enhances the rate of estradiol permeation, said second compound selected from unsaturated ($C_{12}$–$C_{18}$) fatty acids in a concentration from 1 to 20 wt %; and (e) a pharmacologically active progestin in a concentration from 2 to 10 wt %, said weight percentages being based on total weight of said coating layer.

3. A device according to claim 1, wherein the amount of estradiol in the coating layer exceeds the saturation concentration thereof.

4. A device according to claim 1, wherein a pharmaceutically active progestin is includes in a concentration from 2 to 10 wt %.

5. A device according to claim 1, wherein said coating layer comprises in an homogeneous mixture;

i) an adhesive material selected from silicones, acrylic or methacrylic polymers, natural and synthetic rubber and mixtures thereof; and ii) a reinforcing component selected from polyterpenes, modified colophony resins and mixtures thereof.

6. A device according to claim 1, wherein said rate enhancing component comprises as enhancer oleic acid and propylene glycol as inhibitor of oxidation in ratio of 1:0,5 to 1:5.

7. A device according to claim 6, wherein the ratio is 1:1,5.

8. A device according to claim 1, wherein said flexible substrate is selected from the group consisting of cellulose xanthate, aluminum, a polymer or a laminate.

9. A device according to claim 8, wherein the polymer is selected from the group consisting of polyvinyl chloride, polyvinylidene, polyester or polyethylene.

10. A device according to claim 1, wherein the amount of estradiol in the coating layer is sufficient to maintain its concentration at least at saturation level during predetermined periods of time.

11. A process for manufacturing a transdermal delivery device for estradiol, comprising the steps of providing a coating layer on at least part of one surface of a flexible substrate, said coating layer including:

(a) a dermatologically or pharmacologically acceptable pressure sensitive adhesive material for securing the device to the epidermis;

(b) estradiol homogeneously distributed in said coating layer as a pharmacologically active ingredient;

(c) one compound as an inhibitor of inhibitor of enzymatic oxidation of estradiol to estrone, said compound being selected from the group consisting of glycerin and ($C_3$–$C_6$) alkylene 1,2 diols in a concentration from 0.25 to 30 wt %;

(d) a second compound which enhances the rate of estradiol permeation, said second compound selected from unsaturated ($C_{12}$–$C_{18}$) fatty acids in a concentration from 1 to 20 wt %; and (e) a pharmacologically active progestin in a concentration from 2–10 wt %, said weight percentages being based on total weight of said coating layer; and providing a releasable protective layer which, in the finished device, lies on the opposite side of the coating layer to the flexible substrate.

12. A process according to claim 11, wherein the amount of estradiol in said coating layer is in excess of the saturation concentration therein.

13. A process according to claim 11, wherein the coating layer is provided by coating it on the releasable protective layer, bringing the flexible substrate into contact with the coating layer, then cutting the resultant structure to a required shape and size and packaging in a convenient blister system.

14. A device according to claim 1, wherein the packaging is a blister system, which comprises a thermoformed PVC which is heat sealed with a lacquered aluminum foil.

15. A device of claim 10 wherein said predetermined period of time is up to 4 days.

16. A process according to claim 11, wherein said coating layer includes a progestin in a concentration of 2 to 10 wt %.

17. A device according to claim 2, wherein the amount of estradiol in the coating layer exceeds the saturation concentration thereof.

18. A device according to claim 2, wherein another pharmacologically active agent, a progestin, is includes in a concentration from 2 to 10 wt %.

19. A device according to claim 2, wherein said coating layer comprises in a homogeneous mixture:

an adhesive material selected from silicones, acrylic or methacrylic polymers, natural and synthetic rubber and mixtures thereof;

a reinforcing component selected from polyterpenes, modified colophony resins and mixture thereof.

20. A device according to claim 2, wherein said rate enhancing component comprises oleic acid as an enhancer and propylene glycol as an inhibitor of oxidation in a ratio (oleic acid: propylene glycol) ranging from about 1:0.5 to about 1:5.

21. A device according to claim 2 wherein the packing is a blister system which comprises a thermoformed PVC which is heat sealed with a lacquered aluminum foil.

22. A device according to claim 2, wherein the amount of estradiol in the coating layer is sufficient to maintain its concentration at least at saturation level during predetermined periods of time.

23. A process according to claim 12, wherein the coating layer is provided by coating it on the releasable protective layer, then cutting the resultant structure to a required shape and size and packaging in a blister pack.

24. A device according to claim 2, wherein said estradiol comprises 2 wt %.

25. A device according to claim 2, wherein said compound used as an inhibitor of metabolic oxidation of estradiol comprises 15 wt %.

26. A device according to claim 2, wherein the amount of said second compound which enhances the rate of estradiol permeation comprises 10 wt %.

27. A device according to claim 4, wherein the progestin is selected from the group consisting of levonorgestrel and norethindrone acetate.

28. A process according to claim 16, wherein the progestin is selected from the group consisting of levonorgestrel and norethindrone acetate.

29. A device according to claim 1, wherein said estradiol comprises from 1 to 5 wt %; said inhibitor compound comprises from 0.25 to 30 wt %, said enhancer compound comprises from 1 to 20 wt % and said progestin comprises from 2 to 10 wt %; said weight percentages being based on total weight of the coating layer.

* * * * *